US012429447B2

(12) United States Patent
Takada et al.

(10) Patent No.: US 12,429,447 B2
(45) Date of Patent: Sep. 30, 2025

(54) ELECTRICAL CHARACTERISTIC PARAMETER INSPECTION APPARATUS, ELECTRICAL CHARACTERISTIC PARAMETER INSPECTION METHOD, AND STORAGE MEDIUM

(71) Applicant: Konica Minolta, Inc., Tokyo (JP)

(72) Inventors: Makoto Takada, Takatsuki (JP); Junichi Jono, Tokyo (JP); Masaru Fuse, Ibaraki (JP)

(73) Assignee: KONICA MINOLTA, INC., Tokyo (JP)

( * ) Notice: Subject to any disclaimer, the term of this patent is extended or adjusted under 35 U.S.C. 154(b) by 236 days.

(21) Appl. No.: 18/184,200

(22) Filed: Mar. 15, 2023

(65) Prior Publication Data
US 2023/0314355 A1 Oct. 5, 2023

(30) Foreign Application Priority Data
Mar. 31, 2022 (JP) .................. 2022-058147

(51) Int. Cl.
G01N 27/04 (2006.01)
G01N 27/02 (2006.01)
G01N 33/38 (2006.01)

(52) U.S. Cl.
CPC ......... *G01N 27/041* (2013.01); *G01N 33/383* (2013.01); *G01N 27/026* (2013.01)

(58) Field of Classification Search
CPC .. G01N 27/041; G01N 33/383; G01N 27/026; G01N 27/04; G01N 27/00; G01R 31/00
USPC ........................................................ 324/650
See application file for complete search history.

(56) References Cited

U.S. PATENT DOCUMENTS

| 2010/0231213 A1* | 9/2010 | Nieuwenhuis ....... G01R 33/007 324/252 |
| 2011/0240488 A1* | 10/2011 | Lemaire ............ G01N 27/4074 205/785.5 |
| 2015/0137831 A1 | 5/2015 | Pluta et al. |
| 2016/0273995 A1* | 9/2016 | Dandekar ............. G01M 3/182 |

(Continued)

FOREIGN PATENT DOCUMENTS

| JP | 2010-210588 A | 9/2010 |
| JP | 2020-139819 A | 9/2020 |

OTHER PUBLICATIONS

Extended European Search Report dated Aug. 31, 2023, for corresponding Application No. 23165360.1.

(Continued)

*Primary Examiner* — Raul J Rios Russo
(74) *Attorney, Agent, or Firm* — LUCAS & MERCANTI, LLP

(57) ABSTRACT

An electrical characteristic parameter inspection apparatus includes multiple sensors to be arranged on or over an object and a hardware processor. The hardware processor selects multiple predetermined selection patterns, each of the selection patterns including a sensor pair, the sensor pair including two or more sensors among the multiple sensors; measures electrical characteristic parameters for the respective selection patterns, the electrical characteristic parameters being output from the sensors included in the selection patterns; and analyzes the electrical characteristic parameters measured for the respective selection patterns.

20 Claims, 8 Drawing Sheets

(56) References Cited

U.S. PATENT DOCUMENTS

2017/0049356 A1    2/2017  Wang
2017/0131150 A1*   5/2017  Thies ...................... G01K 1/08
2017/0342459 A1*  11/2017  Knopfmacher ...... A61B 5/1486
2019/0216358 A1    7/2019  Gregory

OTHER PUBLICATIONS

Office Action, dated May 13, 2025, which was issued for the corresponding Japanese Patent Application No. 2022-058147, 14 pages, with English translation.
Office Action, dated Jul. 15, 2025, which was issued for the corresponding European Patent Application No. 23165360.1, 4 pages.

* cited by examiner

ELECTRICAL CHARACTERISTIC PARAMETER INSPECTION APPARATUS, ELECTRICAL CHARACTERISTIC PARAMETER INSPECTION METHOD, AND STORAGE MEDIUM

CROSS-REFERENCE TO RELATED APPLICATIONS

The entire disclosure of Japanese Patent Application No. 2022-058147 filed on Mar. 31, 2022 is incorporated herein by reference in its entirety.

TECHNICAL FIELD

The present disclosure relates to an electrical characteristic parameter inspection apparatus, an electrical characteristic parameter inspection method, and a storage medium.

DESCRIPTION OF THE RELATED ART

Reinforced concrete has a high level of toughness at the time of production/construction and is often used to build large-scale buildings and infrastructures (e.g., bridges, roads). However, its toughness greatly decreases owing to corrosion of inside rebars caused by characteristic changes of concrete over time and entrance of water. In recent years, in view of environmental and energy issues, composite fiber reinforced resin (e.g., carbon fiber reinforced plastics (CFRP)) has also been used widely as a structural material of relatively large facilities/buildings and bodies of mobile objects (e.g., aircrafts, automobiles). Such a composite material is advantageous in that it is lighter and tougher than other materials such as metals. However, it has been pointed out that the composite material may deteriorate over time and cause a major breakage/rupture if the material has tiny voids or internal peeling when manufactured. To efficiently evaluate and guarantee the safety and reliability of infrastructures, large-scale buildings, and mobile objects, nondestructive inspections are conducted.

Consumers have become more mindful of product safety in recent years, and regulations have been tightened as a result. There has been a growing social trend to require higher levels of safety for general consumer goods including foodstuffs. Therefore, a simple and easy nondestructive inspection method for evaluating qualities of these goods is awaited.

Conventional nondestructive inspections often rely on expertise of professionals or large manpower (e.g., hammering tests, visual inspections). Such conventional inspection methods have many challenges in terms of efficiency and difficulty in maintaining and handing over the expertise. Therefore, a more efficient and quantitative nondestructive inspection method is awaited.

As an efficient and quantitative nondestructive inspection method for a large and wide object, electromagnetic methods have been proposed and applied to practical uses. Typical electromagnetic methods include the impedance inspection method and the eddy current inspection method, for example. In these methods, a relatively small sensor(s) or the like is put on the surface of an object; an electric field or current is applied to the sensor; and electrical or magnetic characteristics are measured to grasp the structure of the object and the state inside the object. For example, as shown in FIG. 14, according to the impedance inspection method, two electrodes E are attached to an object C (e.g., reinforced concrete); either or both of the electrodes E are moved in the direction of arrows on the object C; and the impedance between the electrodes E is measured. Based on changes in the measured impedance, the structure and the state inside the object C (e.g., corrosion of rebars inside the reinforced concrete) are obtained.

Further, JP2010-210588A discloses a method for detecting a structure buried in the object and the position of the buried structure, based on the difference between multiple impedances measured by multiple electrode pairs selected from a group of electrodes.

SUMMARY OF THE INVENTION

According to the method shown in FIG. 14, a small electrode E is moved on the surface or in the vicinity of the surface of the object C, and the area to be inspected at one time is limited. In order to inspect a large object (e.g., infrastructure), the method requires a mechanism for moving the electrode and takes a long time to move the electrode and to inspect the whole object. Thus, the method has many challenges in terms of efficiency.

Such challenges are common to the method disclosed in JP2010-210588A, in which electrodes are moved to measure impedances at the respective positions; and a buried structure is detected based on the values of impedances at the respective positions of the electrodes.

Although the above challenges are common among apparatuses/methods for inspecting the internal state of an object, the challenges are in particular problematic in inspecting a relatively wide and large object.

Furthermore, in the impedance measurement, measured impedances vary greatly depending on the object. The dynamic range of impedance is extremely wide because the object may be made of an almost insulator (e.g., concrete) or an almost electric conductor (e.g., CFRP). It is therefore difficult to configure a circuit that can measure impedances accurately by diminishing the effect of differences in objects and measuring environments. As a result, a measurement apparatus becomes expensive.

In view of the above, an object of the present invention is to provide an electrical characteristic parameter inspection apparatus, an electrical characteristic parameter inspection method, and a storage medium that can inspect objects efficiently and accurately with low-cost without mechanical scanning.

To achieve the above object, according to an aspect of the present invention, there is provided an electrical characteristic parameter inspection apparatus including: multiple sensors to be arranged on or over an object; and a hardware processor that selects multiple predetermined selection patterns, each of the selection patterns including a sensor pair, the sensor pair including two or more sensors among the multiple sensors; measures electrical characteristic parameters for the respective selection patterns, the electrical characteristic parameters being output from the sensors included in the selection patterns; and analyzes the electrical characteristic parameters measured for the respective selection patterns.

According to an aspect of the present invention, there is provided an electrical characteristic parameter inspection apparatus including: multiple electrode terminals to be arranged on or over a front surface and/or a back surface of an object; and a hardware processor that forms an electrode, the electrode including at least two element electrodes, each of the element electrodes including at least one electrode terminal among the multiple electrode terminals, and forms selection patterns each of which includes multiple electrodes; outputs a predetermined electric signal; brings the electrodes included in each of the selection patterns into contact with or close to the object, applies the output electric signal to the electrodes, and measures an electrical characteristic parameter; and analyzes electrical characteristic parameters measured for the respective selection patterns.

According to an aspect of the present invention, there is provided an electrical characteristic parameter inspection method including: arranging two or more sensors on or over an object in a predetermined selection pattern among multiple selection patterns; measuring an electrical characteristic parameter output from the sensors arranged in the predetermined selection pattern; and analyzing the measured electrical characteristic parameter, wherein the measuring measures the electrical characteristic parameter each time the arranging changes the selection pattern, and the analyzing analyzes electrical characteristic parameters measured for the respective selection patterns.

According to an aspect of the present invention, there is provided an electrical characteristic parameter inspection method including: arranging an electrode pair on or over a front surface and/or a back surface of an object in a predetermined selection pattern among multiple selection patterns; measuring an electrical characteristic parameter by bringing electrodes included in the selection pattern into contact with or close to the object and by applying a predetermined electric signal to the object; and analyzing the measured electrical characteristic parameter, wherein the measuring measures the electrical characteristic parameter each time the arranging changes the selection pattern, and the analyzing analyzes electrical characteristic parameters measured for the respective selection patterns.

According to an aspect of the present invention, there is provided a nontransitory computer-readable storage medium storing a program for a computer of an electrical characteristic parameter inspection apparatus that includes multiple sensors to be arranged on or over an object, the program causing the computer to: select multiple predetermined selection patterns, each of the selection patterns including two or more sensor pairs among the multiple sensors; measure electrical characteristic parameters for the respective selection patterns, the electrical characteristic parameters being output from sensors included in the selection patterns; and analyze the electrical characteristic parameters measured for the respective selection patterns.

According to an aspect of the present invention, there is provided a nontransitory computer-readable storage medium storing a program for a computer of an electrical characteristic parameter inspection apparatus that includes multiple electrode terminals to be arranged on or over a front surface and/or a back surface of an object, the program causing the computer to: form an electrode including at least one element electrode, the element electrode including two or more electrode terminals among the multiple electrode terminals, and form selection patterns each of which includes multiple electrodes; output a predetermined electric signal; bring the electrodes included in each of the selection patterns into contact with or close to the object, apply the output electric signal to the electrodes, and measure an electrical characteristic parameter; and analyze electrical characteristic parameters measured for the respective selection patterns.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION

Embodiments of the present invention are described. The scope of the invention is not limited to the illustrated examples and includes forms and configurations equivalent thereto.

Figure 1:
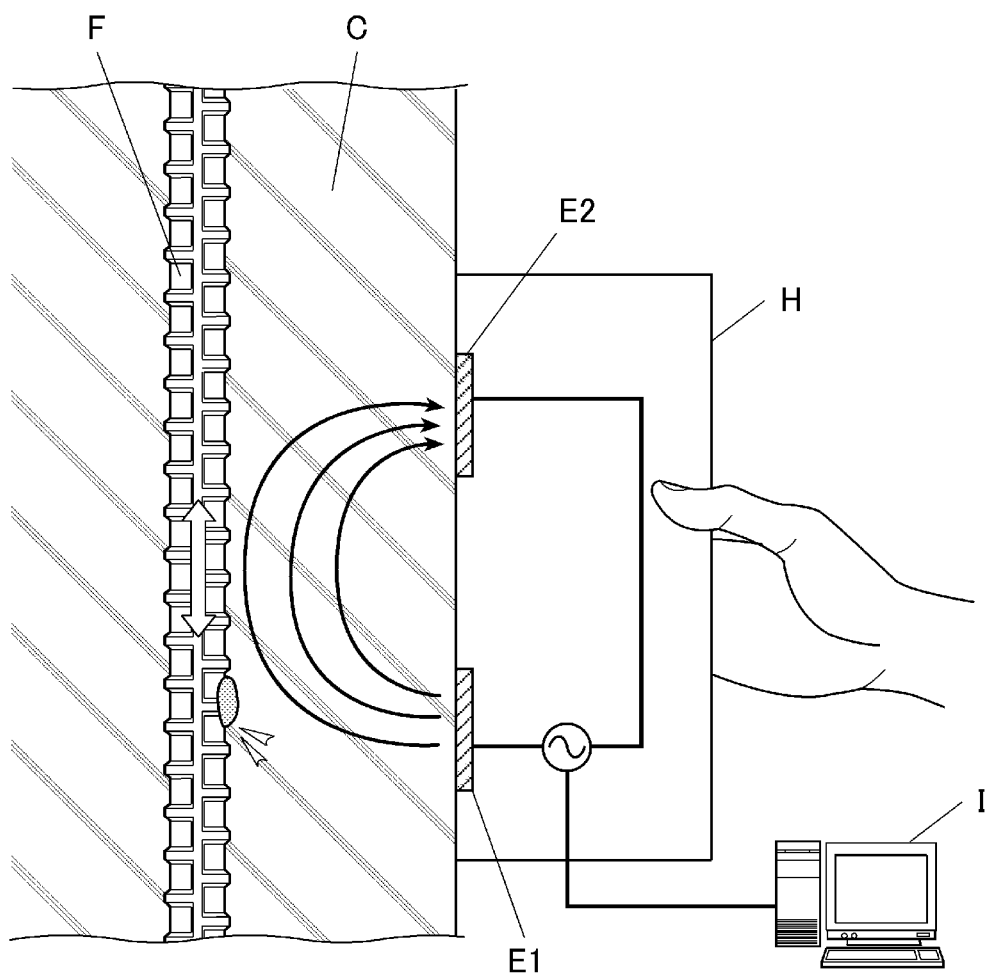
FIG. 1 is a figure to explain a nondestructive inspection method by an electrical characteristic parameter inspection apparatus.

FIG. 1 shows a nondestructive inspection method by an electrical characteristic parameter inspection apparatus 1. A person who performs measurement holds the handle H and brings a first electrode E1 and a second electrode E2 into contact with an object C to measure an electrical characteristic parameter between the first electrode E1 and the second electrode E2, for example.

In FIG. 1, the person holds the handle H and moves the first electrode E1 and the second electrode E2. However, in the following embodiments, the selector 111 selects an electrode(s) E that is to be in contact with the object C.

The configuration of the electrical characteristic parameter inspection apparatus 1 and the processing flow by the electrical characteristic parameter inspection apparatus 1 are the same as in the first embodiment described below.

There may be two or more first electrodes E1 and two or more second electrodes E2.

First Embodiment

Figure 2:
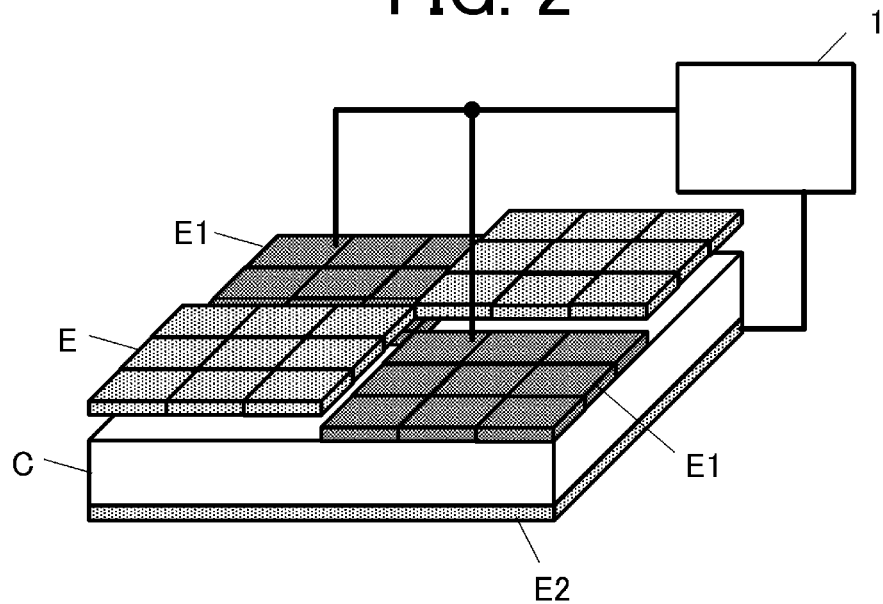
FIG. 2 is a figure to explain a schematic configuration of a measuring system including an electrical characteristic parameter inspection apparatus according to a first embodiment of the present invention.

FIG. 2 shows a schematic configuration of the electrical characteristic parameter inspection apparatus 1 in the first embodiment and the object C.

The electrical characteristic parameter inspection apparatus 1 holds the object C between the first electrode E1 and the second electrode E2 that are in contact with or that are close to the object C. This arrangement of electrodes is called the out-plane arrangement. The electrical characteristic parameter inspection apparatus 1 thus measures the value of the electrical characteristic parameter of the object C between the first electrode E1 and the second electrode E2. Although one second electrode E2 covers the entire bottom surface of the object in FIG. 2, individual second electrodes E2 corresponding to individual first electrodes E1 may be provided. In view of such a configuration, a pair of a first electrode E1 and a second electrode E2 is called an electrode pair. The second electrode E2 may not be on the bottom surface of the object C but may be inside the object C.

A typical example of the object C is a relatively large structure, such as reinforced concrete (rebar F in FIG. 1), but the object C is not limited to this. Other examples of the object C include a semiconductor, an insulator, a conductor, a material that has changeable electrical characteristics depending on the environment, a metal structure, a composite material made of filler and resin (e.g., CFRP), and a composite material made of metal or resin. The electrical characteristic parameter inspection apparatus 1 obtains electrical characteristic parameters in order to inspect the structure of the object, examine the characteristic and the state of the object, and detect a defect of the object (e.g., foreign objects, cracks, peeled parts, voids).

Following are definitions of terms. An electrode terminal refers to a single electrode terminal. An element electrode includes two or more electrode terminals. The polarity of applied voltage is not distinguished. Multiple element electrodes are required to form an element area. An electrode refers to all the element electrodes and electrode terminals that are required to form one element area (measurement region). An element area refers to the distribution of an electric field that occurs between multiple electrodes/element electrodes. The element area is the actual measurement region. An electrode pair refers to electrodes that create a voltage difference.

Figure 3:
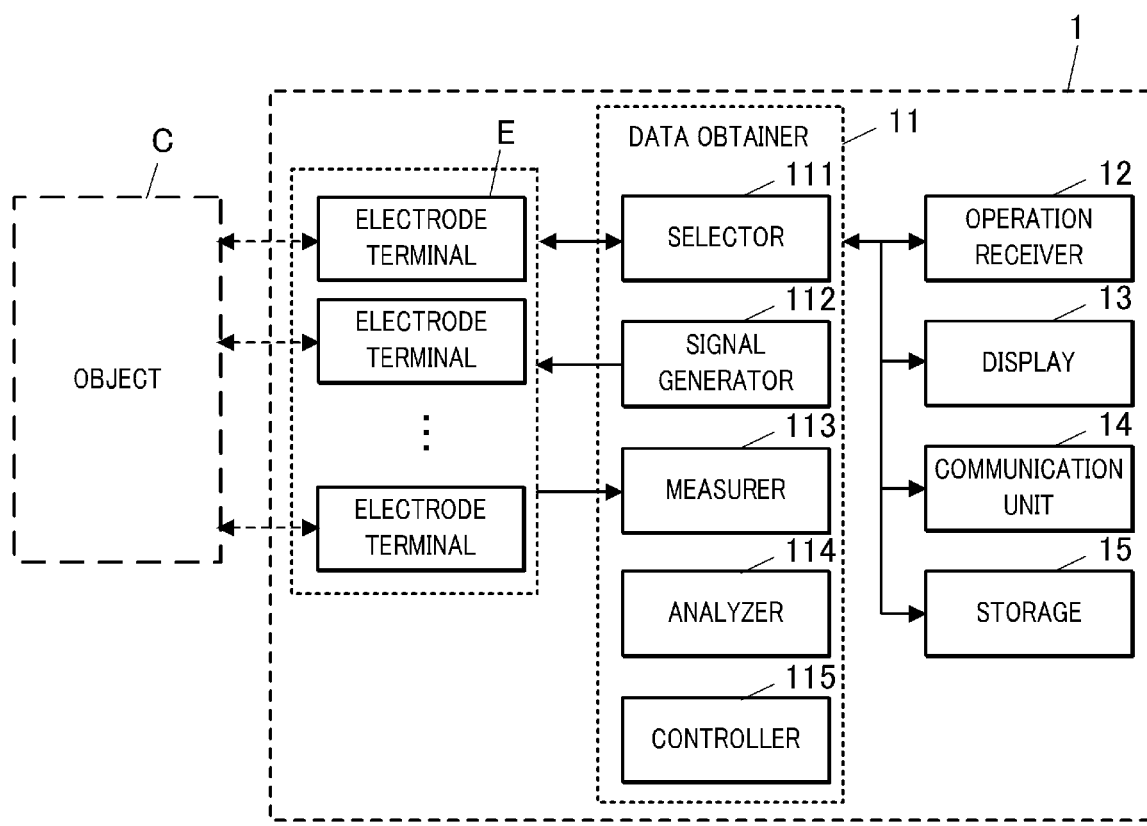
FIG. 3 is a block diagram showing functional components of the electrical characteristic parameter inspection apparatus according to the first embodiment of the present invention.

FIG. 3 is a block diagram showing functional components of the electrical characteristic parameter inspection apparatus 1. The electrical characteristic parameter inspection apparatus 1 includes a data obtainer 11 (hardware processor), an operation receiver 12, a display 13, a communication unit 14, a storage 15, and electrodes E.

The data obtainer 11 includes a central processing unit (CPU) and a random access memory (RAM). The data obtainer 11 executes and controls a series of data obtaining operations by the electrical characteristic parameter inspection apparatus 1. More specifically, the CPU reads various processing programs stored in the storage 15, loads them into the RAM, and performs various processes in cooperation with the programs. The data obtainer 11 functions as a selector 111, a signal generator 112, a measurer 113, an analyzer 114, and a controller 115.

The selector 111 selects a predetermined pair(s) of electrodes from multiple electrode pairs facing the object C. The selector 111 brings the selected electrode pair into contact with the object C or brings the selected pair close to the object C. The selector 10 includes a not-illustrated mechanism that brings the electrode pair into contact with or close to the object C and that separates the electrode pair from the object C. Each of the electrodes may be constituted of a group of electrode terminals.

In FIG. 2, the selector 111 of the electrical characteristic parameter inspection apparatus 1 selects the first electrodes E1 and brings the first electrodes E1 into contact with the object C. That is, in FIG. 2, the selector 111 selects (i) nine (3×3) electrodes/electrode pair E in the left back and (ii) nine (3×3) electrodes/electrode pair E in the right front as the first electrodes E1; and the selector 111 brings the selected electrodes/electrode pairs E into contact with the object C. The pattern of selected electrodes or selected electrode pairs E is called a selection pattern. The selector 111 switches and controls the positions and sizes of electrodes/electrode pairs. Although the second electrode E2 in FIG. 2 covers the entire bottom surface of the object C (the surface opposite to the surface in contact with the first electrodes E1), the configuration of the second electrode E2 is not limited to this. There may be individual second electrodes E2 that are sized and positioned to correspond to the individual first electrodes E1.

Figure 4:
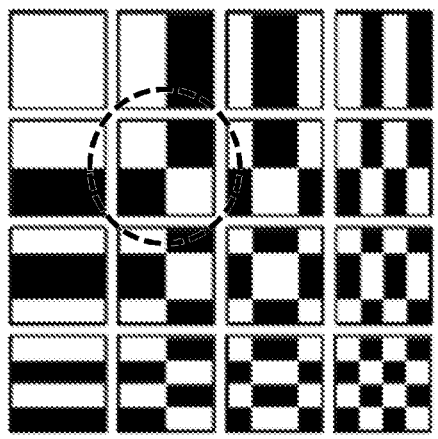
FIG. 4 is an example of an electric field pattern formed by the electrical characteristic parameter inspection apparatus in the present invention.

An electric field pattern is spatially formed by applying electric signals to the first electrode E1 and the second electrode E2. An electric field pattern is a predetermined two-dimensional pattern that is formed on a two-dimensional plane in a bird's-eye view from above the object. For example, FIG. 4 shows two-dimensional patterns that are orthogonal to each other in a two-dimensional space. For example, the electric field pattern circled by the dashed line in FIG. 4 is formed by the electrodes arranged as shown in FIG. 2. When the electrodes/electrode pair E (first electrodes E1) are brought into contact with the object C and signals are applied, an electric field is formed. In FIG. 4, white regions in the two-dimensional patterns indicate regions in which an electric field is formed and an electric parameter is obtained, whereas black regions indicate regions in which an electric field is not formed. In the electric field patterns, the region that corresponds to each electrode or each electrode pair E is called an element area A. Predetermined two-dimensional patterns orthogonal to each other may be an Hadamard matrix cycle pattern. Predetermined two-dimensional patterns may also be a random pattern.

The signal generator 112 outputs electric signals (AC signals) swept within a predetermined frequency range to the electrode pair that includes the first electrode E1 and the second electrode E2.

When AC signals are used, the signal generator 112 regulates the frequency, the frequency range, and the AC signal amplitude (AC voltage amplitude, AC current amplitude) of the AC signals applied to the electrode pair.

The measurer 113 measures the value of electrical characteristic parameter at the time the electric signals, which are output from the signal generator 112, are applied to the electrode pair. Examples of the electrical characteristic parameter include a current value, a voltage value, an impedance, an admittance, and a permittivity and a conductivity derived therefrom.

The controller 115 controls the selector 111, the signal generator 112, and the measurer 113 to change the selection pattern and to measure electrical characteristic parameters for the respective selection patterns. The controller 115 obtains and accumulates the electrical characteristic parameters measured for the respective selection patterns. For example, the controller 115 obtains the electrical characteristic parameters for the respective selection patterns shown in FIG. 4.

The analyzer 114 analyzes values of electrical characteristic parameters measured for the respective selection patterns.

For example, the electrodes/electrode pairs shown in FIG. 2 are aligned regularly with respect to the object C so that comprehensive two-dimensional information of the object C is obtained. Each of the selection patterns is for obtaining partial two-dimensional information of the object C. By obtaining electrical characteristic parameters for the respective selection patterns, the information relating to different regions of the object C is obtained.

Here, electrical characteristic parameters measured for the respective selection patterns are an accumulation of information obtained from multiple electrode pairs in the selection patterns. Therefore, the two-dimensional information of the object C cannot be obtained from the values of electrical characteristic parameters only. On the other hand, the positions of electrode pairs in each selection pattern are known. As described above, each of the measured values corresponding to each of the selection patterns includes information on a different area of the object C and includes signal information of each frequency band used for the measurement (e.g., amplitude, phase).

Next, the analyzer 114 reconstructs the two-dimensional information of the object C by performing matrix calculation with (i) known positional information of electrode pairs in the respective selection patterns and (ii) electrical characteristic parameters measured for the respective selection patterns. To efficiently perform matrix calculation, an Hadamard matrix cycle pattern or a random pattern is used as the selection pattern. The reconstructed two-dimensional information of the object C indicates the distribution of resistances, permittivities, or capacitances in the object C, for example. The reconstructed two-dimensional information of the object C may also be an existence probability or positional information of a defect, a foreign object, or a corroded part in the object C.

Multiple selection patterns are required for measurement in order to reconstruct the two-dimensional information of the object C. Basically, the greater the number of selection patterns used in measurement is, the higher the accuracy of the reconstruction is, and the longer the measurement time is. In performing calculation to reconstruct the two-dimensional information, the analyzer 114 analyzes information obtained from measurements each time the measurement is performed by applying a statistical method or machine learning. The analyzer 114 continues to perform measurement until obtaining a desired level of accuracy for the purpose (e.g., regression, classification). Thus, the measurement is performed in an appropriate period of time.

In FIG. 2, electrodes/electrode pairs are arranged next to each other in a rectangular pattern. However, the arrangement of electrodes is not limited to this as long as the combinations of electrodes/electrode pairs in the respective selection patterns are known. For example, electrodes/electrode pairs may be arranged in a circle, may be interspersed at separate positions, or may not be on the same plane.

The information to be analyzed by the analyzer 114 is not limited to the reconstructed two-dimensional information but may be the values themselves measured for the respective selection patterns. Since the positions of electrodes/electrode pairs in the respective selection patterns are known, an approximate position of an abnormal part in the object C can be estimated when the analysis result of a value measured for a selection pattern indicates abnormality. Based on the obtained information, the measurement procedure (algorithm) is appropriately adjusted so as to select selection patterns that are likely to correspond to an abnormal part. Thus, an accurate measurement is performed in a shorter period of time.

According to such a method, the analyzer 114 can identify the position of a defect in the object C in a short time without a statistical method or machine learning by gradually narrowing regions having high (or low) electrical characteristic parameters.

The operation receiver 12 includes: a keyboard including cursor keys, character entry keys, and various function keys; and a pointing device, such as a mouse. The operation receiver 12 outputs operation signals input by the manipulation of the keyboard or the mouse to the data obtainer 11. The operation receiver 12 may include a touchscreen and output operation signals corresponding to the position touched by the finger of the operator to the data obtainer 11.

The display 13 includes a monitor, such as a liquid crystal display (LCD), and displays various contents in accordance with display signals input by the data obtainer 11.

The communication unit 14 includes a network interface, for example. The communication unit 14 sends and receives data to and from external apparatuses connected over the communication network N, such as a LAN, a wide area network (WAN), or the internet.

The storage 15 includes a hard disk drive (HDD) and/or a nonvolatile semiconductor memory, for example. The storage 15 stores various kinds of data.

Electrodes and electrode pairs E are elements that convey electric signals output by the signal generator 112 to the object C. Electrodes and electrode pairs E may be flat-plate-shaped or film-shaped, for example. As described above, in FIG. 2, electrode pairs are constituted of (i) the first electrodes E1 selected by the selector 111 and in contact with the surface of the object C and (ii) the second electrode E2 in contact with the bottom surface of the object C.

Here, multiple electrode pairs selected for the respective selection patterns are connected in an appropriate manner depending on the object. With respect to an object that has a rather high impedance (e.g., concrete), electrode pairs, each of which includes a first electrode E1 and a second electrode E2, are connected in parallel. With respect to an object that has a rather low impedance (e.g., CFRP), electrode pairs are connected in series. Specifically, as a modification of FIG. 2, a second electrode E2 is a selected electrode E that faces a first electrode E1 with the object C inbetween. Multiple electrode pairs each including a first electrode E1 and a second electrode E2 are connected in series in the order of a first electrode E1, a second electrode E2, a first electrode E1, . . . . Thus, the dynamic range of electrical characteristic parameters input to the measurer 113 is narrowed, and the electrical specification required for the measurer 113 is relieved.

Figure 5:
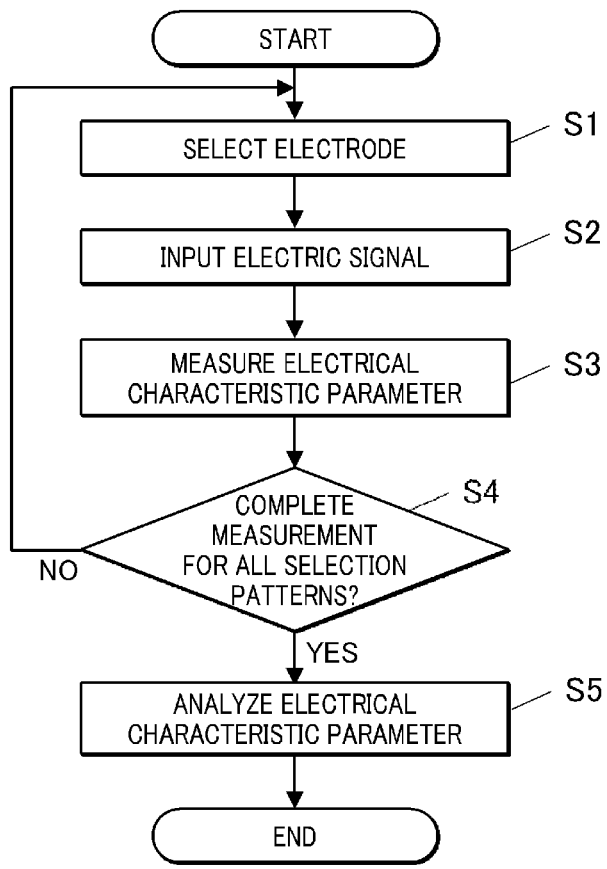
FIG. 5 is a flowchart showing a processing method by the electrical characteristic parameter inspection apparatus according to the first embodiment of the present invention.

FIG. 5 is a flowchart of a processing method by the electrical characteristic parameter inspection apparatus 1.

In the processing method shown in FIG. 5, the electrical characteristic parameter inspection apparatus 1 selects electrodes/electrode pairs E based on predetermined selection patterns, obtains and analyzes electrical characteristic parameters for the respective selection patterns, and obtains the distribution of electrical characteristic parameters in the object C as two-dimensional information. Multiple selection patterns are stored in the storage 15 beforehand. The measurement target region of the object C is entirely covered by switching the selection patterns.

The selection patterns may be switched randomly, or the switching order may be determined as desired depending on the usage or the purpose. For example, consider a case where the measurement is performed by using electrodes/electrode pairs that are arranged two-dimensionally as shown in FIG. 2, based on the Hadamard matrix cycle pattern, as shown in FIG. 4. In the case, the measurement is started with a low spatial frequency pattern and proceeded with gradually higher frequencies. Accordingly, approximate two-dimensional information of the object C can be obtained at an early stage in the process of reconstruction, and the measurement can be efficiently conducted.

The selector 111 selects one or more electrodes based on predetermined selection patterns and brings the selected electrode(s) into contact with the object C (Step S1). In the configuration shown in FIG. 2, the second electrode E2 (element electrode) has already been in contact with the entire bottom surface of the object C. Therefore, the selector 111 selects the first element electrodes E1 only and brings the first element electrodes E1 into contact with the object C.

The signal generator 112 inputs electric signals to the electrode pair constituted of the first electrode E1 and the second electrode E2 (Step S2).

The measurer 113 measures the electrical characteristic parameter (e.g., impedance) in the region of the object C by using the first electrode E1 and the second electrode E2 (Step S3).

The controller 115 instructs the selector 111 to change the selection pattern and centrally controls the selector 111, the signal generator 112, and the measurer 113 to repeat the process from Step S1 to Step S3. The operations and functions of the controller 115 may not be carried out automatically by a computer but may be carried out by a measuring person. Specifically, the person may artificially select/change the selection pattern to repetitively obtain the electrical characteristic parameter.

The data obtainer 11 determines whether the predetermined measurement has been performed by using predetermined multiple selection patterns stored in the storage 15 (Step S4). When determining that the predetermined measurement has been completed (Step S4: YES), the data obtainer 11 proceeds to analyzing of the measured electrical characteristic parameters. When determining that the predetermined measurement has not been completed yet (Step S4: NO), the data obtainer 11 proceeds to Step S1 and performs the measurement with the next selection pattern.

The analyzer 114 analyzes the electrical characteristic parameters obtained for the respective selection patterns (Step S5). For example, the analyzer 114 reconstructs two-dimensional information of the object C by performing matrix calculation based on (i) known positional information of electrode pairs in the respective selection patterns and (ii) electrical characteristic parameters measured for the respective selection patterns. This allows the user to grasp the distribution of electrical characteristic parameters in the object C and check whether internal rebars are corroded.

Figure 6:
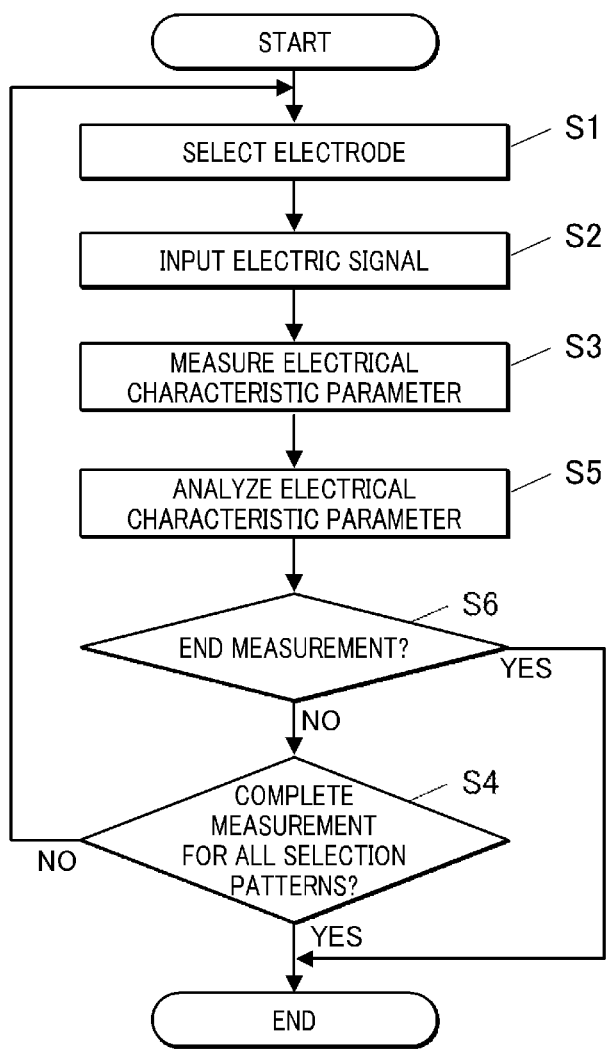
FIG. 6 is a flowchart showing another processing method by the electrical characteristic parameter inspection apparatus according to the first embodiment of the present invention.

FIG. 6 is a flowchart showing another processing method by the electrical characteristic parameter inspection apparatus 1. Steps S1 to S3 in FIG. 6 are the same as in the flowchart in FIG. 5 and are not described here.

The analyzer 114 reconstructs the two-dimensional information by using electrical characteristic parameters obtained in Step S3. The display 13 displays the reconstruction result to the measuring person, and the person is allowed to determine whether to continue or end the measurement in Step S6. Alternatively, the analyzer 114 may determine whether a sufficient level of accuracy has been obtained with respect to the purpose, based on a statistical method or machine learning, and determine whether to continue or end the measurement. According to such a flow, the measurement can be performed at a required level of accuracy in a minimum measurement time.

In the flows shown in FIG. 5 and FIG. 6, inputting electric signals (S2), measuring the electrical characteristic parameter (S3), and analyzing the electrical characteristic parameter (S5) are performed one after another. However, the inputting (S2) and the measuring (S3) based on the next selection pattern may be performed while the analyzing (S5) based on the current selection pattern is performed.

Second Embodiment

Figure 7:
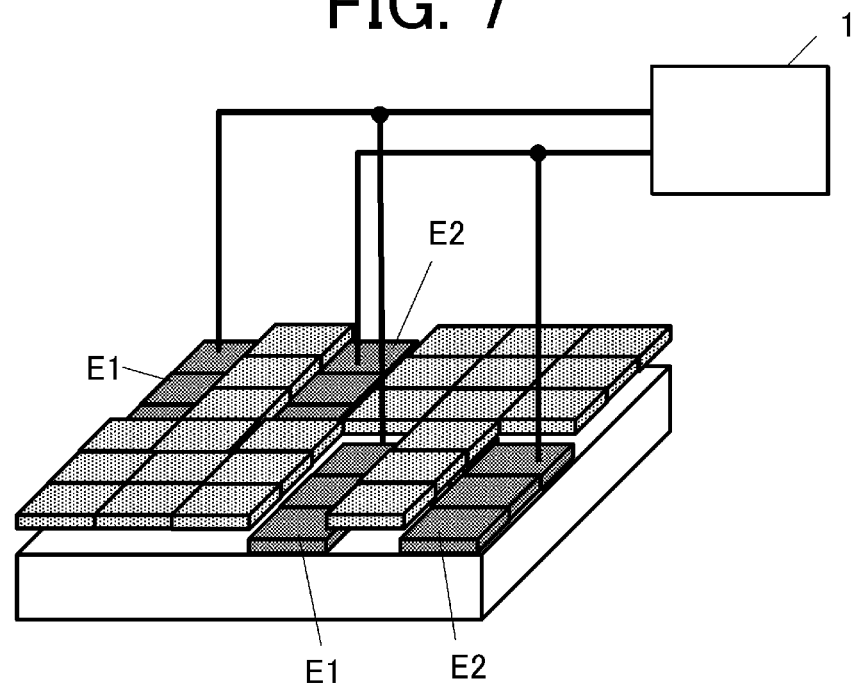
FIG. 7 is a figure to explain a schematic configuration of the electrical characteristic parameter inspection apparatus according to a second embodiment of the present invention.

FIG. 7 shows a schematic configuration of the electrical characteristic parameter inspection apparatus 1 and the object C in the second embodiment.

The electrical characteristic parameter inspection apparatus 1 uses an electrode pair(s) (a first electrode E1 and a second electrode E2) that is in contact with or that is close to the same surface of the object C (the front surface in FIG. 7) to measure the electrical characteristic parameter of the object C between the first electrode E1 and the second electrode E2. This arrangement of electrodes is called an in-plane arrangement.

The electrodes arranged as shown in FIG. 7 form the electric field pattern enclosed in the dashed line in FIG. 4 and obtain the electrical characteristic parameter of the white part in the electric field pattern.

The selector 111 selects an electrode(s) and brings the selected electrode into contact with the object C (Step S1).

The other configuration of the electrical characteristic parameter inspection apparatus 1 and the flow of the process are the same as in the first embodiment.

Third Embodiment

Figure 8:
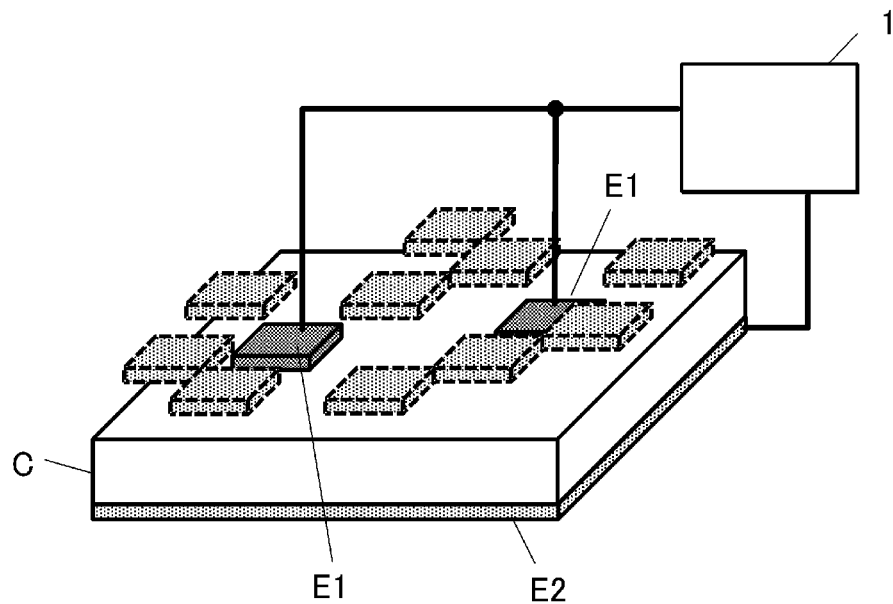
FIG. 8 is a figure to explain a schematic configuration of the electrical characteristic parameter inspection apparatus according to a third embodiment of the present invention.

FIG. 8 shows a schematic configuration of the electrical characteristic parameter inspection apparatus 1 and the object C in the third embodiment.

In the first and second embodiments, all the electrodes/electrode pairs E are arranged in line. However, they may not necessarily be arranged in such a way. Electrodes/electrode pairs may be appropriately arranged as shown in FIG. 8 so as to correspond to the shape of the object or the target region in which an electrical characteristic parameter is to be obtained.

The other aspects of the electrical characteristic parameter inspection apparatus 1 and the flow of the processing method are the same as in the first embodiment.

Electrodes/electrode pairs E of different sizes may be prepared so that the measuring person can select an electrode/electrode pair of an appropriate size therefrom according to the white part in the two-dimensional pattern in FIG. 4. Thus, electrodes can be arranged more flexibly. More specifically, with respect to the electric field pattern in the upper left in FIG. 4, a large electrode(s)/a large electrode pair(s) E is used in the selection pattern. With respect to the electric field pattern in the lower right in FIG. 4, a small electrode (s)/a small electrode pair(s) E is used in the selection pattern. Thus, the number of electrodes/electrode pairs E used in each of the selection patterns can be reduced. This allows the measuring person to flexibly and efficiently arrange electrodes.

OTHERS

Figure 9:
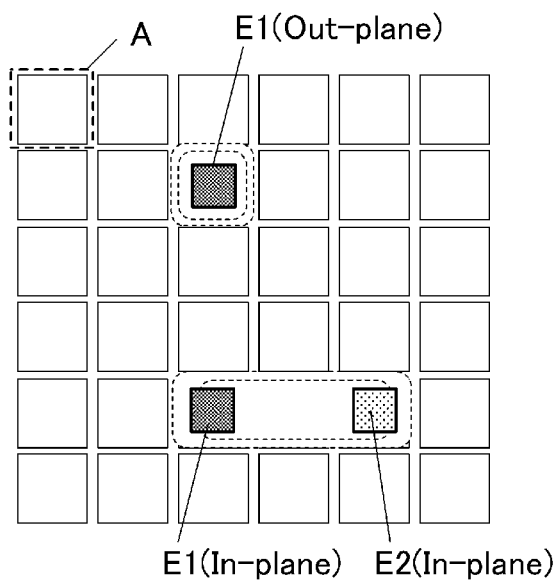
FIG. 9 is a figure to explain the relation between an electrode size and an element area of the electrical characteristic parameter inspection apparatus in the present invention.

FIG. 9 shows the relation between the size of an electrode/electrode pair E and the element area A. An electric field extends beyond an electrode/electrode pair E. In consideration of this, in FIG. 9, the size of an electrode/electrode pair E is smaller than the element area A. Thus, the spread of the electric field is kept within the element area A; the target region of the object C for obtaining the electrical characteristic parameter is appropriately determined; and the resolution is improved for analyzing the distribution of electrical characteristic parameters.

In order to reconstruct the distribution of electrical characteristic parameters in the object C as two-dimensional information based on the selection patterns in FIG. 4 and the electrical characteristic parameters corresponding to the respective selection patterns, it is preferable that an electric field be formed so as to correspond to a selection pattern. When the size of an electrode/electrode pair E is equal to the size of the corresponding element area A, the electric field extends beyond the element area A. This leads to a failure to obtain accurate electrical characteristic parameters corresponding to the respective selection patterns in FIG. 4.

It is preferable that the size of an electrode/electrode pair E be approximately equal to or greater than one fourth of the size of the corresponding element area A (half a side of the element area A), for example.

Figure 10:
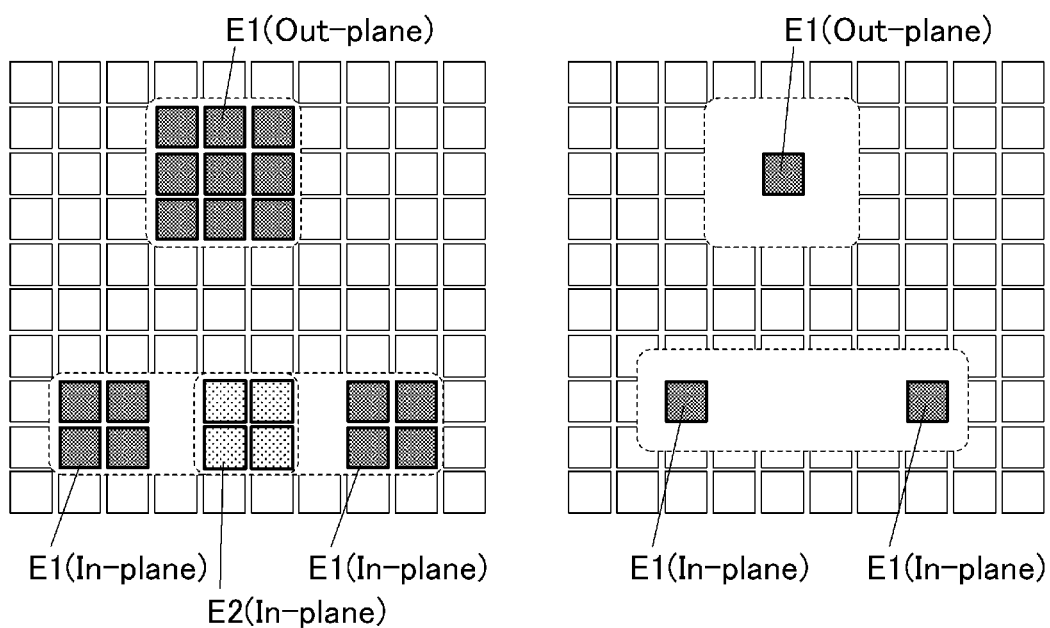
FIG. 10 is a figure to explain the relation between the electric conductivity of an object and an electrode size of the electrical characteristic parameter inspection apparatus in the present invention.

FIG. 10 shows the relation among (i) the size of an electrode pair (a first electrode (s) E1 and a second electrode E2), (ii) the electric field pattern formed by the electrodes, and (iii) the conductivity of the object C. In FIG. 10, parts enclosed by dotted lines represent electric fields formed by the respective electrodes. In order to obtain the electric field pattern shown in FIG. 10, when the conductivity of the object C is high (left in FIG. 10), 3×3 electrodes E having approximately the same size as the electric field pattern are selected. When the conductivity of the object C is low (right in FIG. 10), only one electrode E having a smaller size than the electric field pattern is selected.

When the conductivity of the object C is high, the electric field formed by an electrode does not tend to spread greatly with respect to the electrode size. On the other hand, when the conductivity of the object C is low, the electric field formed by an electrode tends to spread with respect to the electrode size. That is, the effect of an electric field, which extends beyond an electrode size, on the electrical characteristic parameter to be obtained in this embodiment changes depending on the conductivity of the object C. To deal with this, the first electrode E1 and/or the second electrode E2 is constituted of a plurality of element electrodes, and the number of element electrodes constituting the first electrode E1/second electrode E2 is adjusted according to the conductivity of the object C. Thus, the size of the first electrode E1/second electrode E2 is adjusted, and the electric field pattern is appropriately formed in a desired region. This increases the resolution for analyzing the distribution of electrical characteristic parameters.

Figure 11:
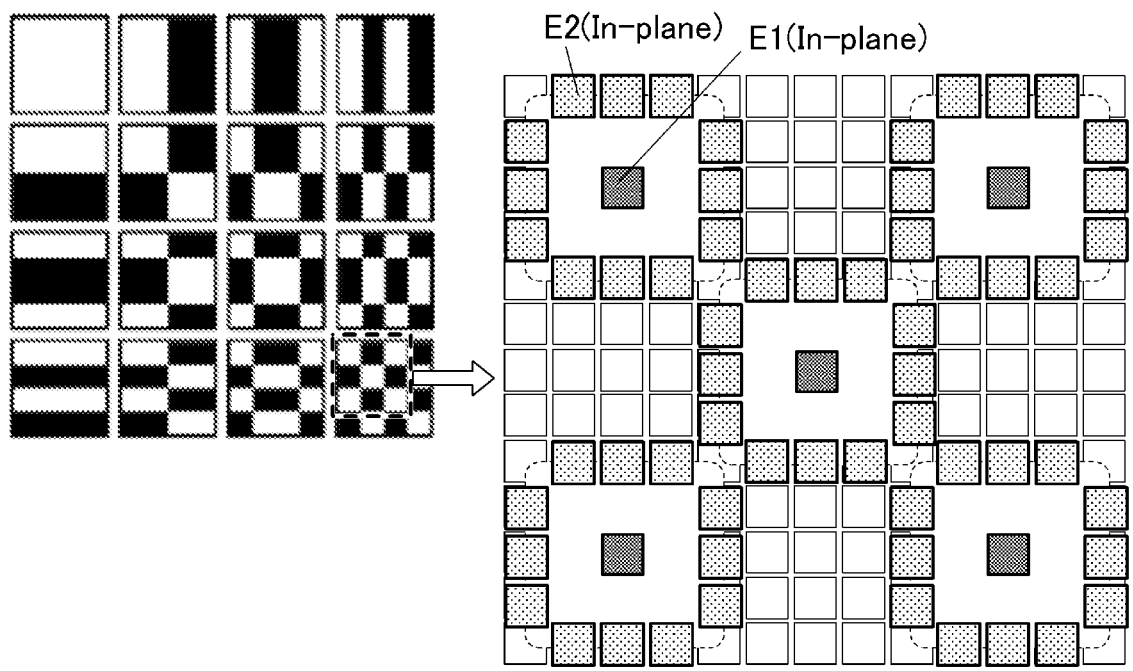
FIG. 11 is an example of an electric field guard band of the electrical characteristic parameter inspection apparatus in the present invention.

FIG. 11 shows a case where an electric field guard band (shielding area) is provided. In cases of the in-place arrangement, a first electrode E1 is enclosed by second electrodes E2, as shown in FIG. 11. Such an arrangement can restrain the spread of the electric field beyond the second electrodes E2. Such an arrangement can prevent mutual interference between electric fields formed by different electrode pairs. Thus, the electric field is formed so as to correspond to the selection pattern, and the resolution is increased for analyzing the distribution of electrical characteristic parameters.

In cases of the out-plane arrangement, ground electrodes connected to the ground are arranged around a first electrode E1 to form a guard band. The ground electrodes are selected by the selector 111.

Figure 12:
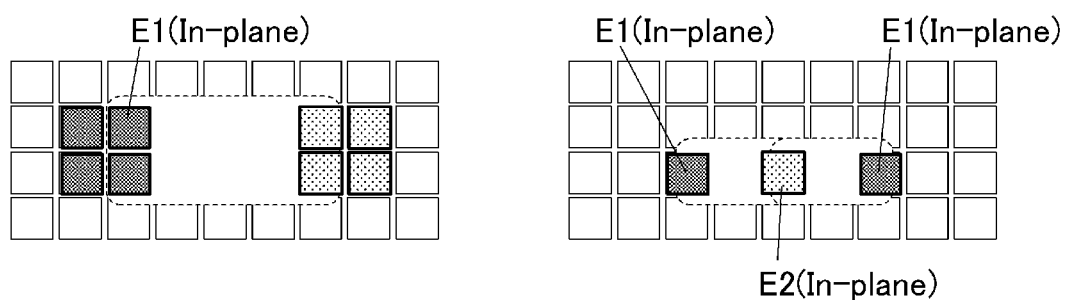
FIG. 12 is a figure to explain the relation between the frequency band of electric signals and the electrode size of the electrical characteristic parameter inspection apparatus in the present invention.
Figure 13A:
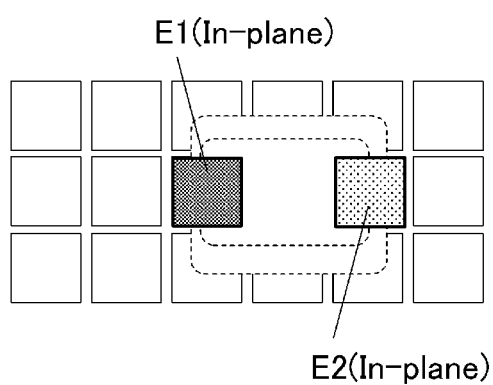
FIG. 13A shows the distribution of the electric field and electrodes of the electrical characteristic parameter inspection apparatus in the present invention.
Figure 13B:
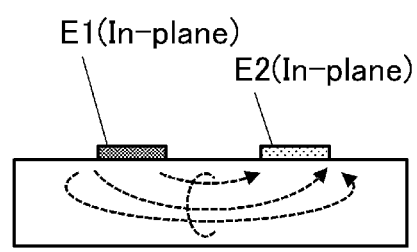
FIG. 13B shows the distribution of an electric field and electrodes of the electrical characteristic parameter inspection apparatus in the present invention.
Figure 14:
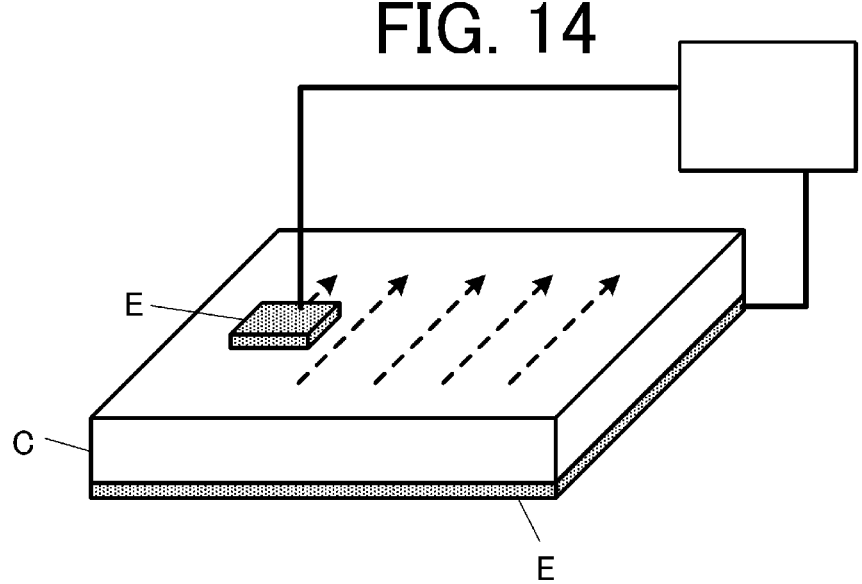
FIG. 14 is a figure to explain a schematic configuration of a known electrical characteristic parameter inspection apparatus.

FIG. 12 and FIG. 13 are figures to explain the relation between (i) a profile (e.g., frequency band) of an electric signal output by the signal generator 112 and (ii) the arrangement of electrodes/the inspection target region of the object C.

FIG. 12 shows (i) the difference in how the electric field spreads depending on the frequency of electric signals output by the signal generator 112 and (ii) the distance between electrodes corresponding to the difference in how the electric field spreads. In a low frequency band, an electric field has a small space attenuation. Therefore, the distance between the first electrode E1 and the second electrode E2 can be wide, as shown in the left of FIG. 12. On the other hand, in a high frequency band, an electric field has a large space attenuation. Therefore, the distance between the first electrode E1 and the second electrode E2 is shorter than in a low frequency band, as shown in the right of FIG. 12.

The signal generator 112 adjusts the frequency range, based on the distance between the first electrode E1 and the second electrode E2. More specifically, when the distance between the first electrode E1 and the second electrode E2 is short, the signal generator 112 sets a high frequency range. When the distance between the first electrode E1 and the second electrode E2 is wide, the signal generator 112 sets a low frequency range.

Alternatively, the selector 111 adjusts the distance between the first electrode E1 and the second electrode E2, based on the frequency range of electric signals output by the signal generator 112. More specifically, when the frequency range of electric signals output by the signal generator 112 is a high frequency band, the selector 111 shortens the distance between the first electrode E1 and the second electrode E2. When the frequency range of electric signals is a low frequency band, the selector 11 widens the distance between the first electrode E1 and the second electrode E2.

FIG. 13 shows the difference in how the electric field spreads in the depth direction depending on the frequency of electric signals output by the signal generator 112 in the in-plane arrangement. In a low frequency band, an electric field has a small space attenuation and reaches deep parts of the object C, and the electrical characteristic parameter in deep parts of the object C can be obtained. On the other hand, in a high frequency band, an electric field has a large space attenuation and is formed in shallow parts of the object C, and the electrical characteristic parameter in shallow parts of the object C can be obtained.

The signal generator 112 adjusts the frequency range of electric signals, based on the depth of inspection in the object C. More specifically, when the target measurement region is shallow in the object C, the signal generator 112 sets the frequency range of electric signals to a high frequency band. When the target measurement region is deep in the object C, the signal generator 112 sets the frequency range of electric signals to a low frequency band.

The shape of electrode terminals is not limited to a film shape but may be a bulk shape, a needle shape, or various other shapes. Electrode terminals may not be rectangular but may be round, triangular, or shapeless. The shape of electrode terminals is determined based on the shape and characteristic of the object C such that electrode terminals can apply appropriate electric fields to the object C. For example, electrode terminals may be made of soft material or uneven material. Such electrodes/electrode pairs can be in contact with or closer to the object C having an uneven surface, and electrical characteristic parameters can be appropriately measured.

Electrodes may be arranged in a combination of the in-plane arrangement and the out-plane arrangement. That is, either the in-plane arrangement or the out-plane arrangement is used for each region of the object C, depending on the shape and the structure of the object C. Thus, electrical characteristic parameters can be flexibly obtained regardless of the shape and the structure of the object.

The signal generator 112 may apply electric signals having different frequency bands to the respective electrodes/electrode pairs. More specifically, the signal generator 112 converts (up-converts or down-converts) the frequency of electric signals, and applies the converted electric signals to the respective electrodes/electrode pairs. In particular, electric signals having different frequency bands are applied to adjacent electrode pairs in order to prevent the interference between electric fields formed by the respective electrodes/electrode pairs. Thus, more accurate electrical characteristic parameters can be obtained.

The signal generator 112 may change the order or the direction of sweeping frequencies of electric signals to be applied, depending on the electrode/electrode pair. For example, with respect to adjacent electrodes or adjacent electrode pairs, the signal generator 112 applies an electric signal that is swept from a low frequency to a high frequency to one electrode/electrode pair, whereas the signal generator 112 applies an electric signal that is swept from a high frequency to a low frequency to the other electrode/electrode pair. This prevents the interference between electric fields formed by the adjacent electrodes/electrode pairs, and more accurate electrical characteristic parameters can be obtained.

The signal generator 112 may not apply an electric signal having one frequency component but may apply an electric signal having multiple frequency components to an electrode/electrode pair. The measurer 113 may simultaneously measure multiple electrical characteristic parameters for multiple frequency components. Thus, electrical characteristic parameters can be obtained in a shorter period of time. The measurer 113 extracts electrical characteristic parameters for the respective frequency components by applying filtering or fast Fourier transform, for example.

Electrodes/electrode pairs E may be configured to resonate in a predetermined frequency band. This can improve the sensitivity for obtaining electrical characteristic parameters in a predetermined frequency band.

A signal applied to electrodes/electrode pairs may be an AC signal on which a DC signal is superposed as a bias. To superpose a DC signal, the signal generator 112 controls DC voltage and DC current. Thus, the DC bias dependence of electrical characteristic parameters of the object C can be measured. In order to obtain impedance as electrical characteristic parameters, the impedance is calculated based on the input/output signal from which the DC signal is subtracted.

In the above embodiments, electric signals are applied to the object C via electrode pairs. As a different embodiment, a sensor may detect a signal output by the object C (e.g., radiation, magnetic force, temperature). In such an embodiment, it is not necessary to apply a signal to the sensor. Examples of the sensor include a radiation detector, a magnetic force sensor, and a temperature sensor.

ADVANTAGEOUS EFFECT

As described above, the electrical characteristic parameter inspection apparatus 1 includes: multiple sensors to be arranged on or over an object; the selector 111 that selects multiple selection patterns, each of the selection patterns including a sensor pair, the sensor pair including two or more sensors among the multiple sensors; the measurer 113 that measures electrical characteristic parameters for the respective selection patterns, the electrical characteristic parameters being output from the sensors included in the selection patterns; and the analyzer 114 that analyzes the electrical characteristic parameters measured for the respective selection patterns. According to such a configuration, the electrical characteristic parameter inspection apparatus 1 can efficiently inspect an object having a wide region without mechanical scanning.

Further, the electrical characteristic parameter inspection apparatus 1 includes: multiple electrode terminals to be arranged on or over a front surface and/or a back surface of an object; the selector 111 that forms an electrode, the electrode including at least two element electrodes, each of the element electrodes including at least one electrode terminal among the multiple electrode terminals, and forms selection patterns each of which includes multiple electrodes; the signal generator 112 that outputs a predetermined electric signal; the measurer 113 that brings the electrodes included in each of the selection patterns into contact with or close to the object, applies the electric signal output by the signal generator 112 to the electrodes, and measures an electrical characteristic parameter; and the analyzer 114 that analyzes electrical characteristic parameters measured for the respective selection patterns. According to such a configuration, the electrical characteristic parameter inspection apparatus 1 can efficiently inspect an object having a wide region without mechanical scanning.

Preferably, based on an electrical characteristic of the object, the measurer 113 may determine a measurement target region of the object as an element area, the element area corresponding to the electrode, and measure the electrical characteristic parameter of the element area. Such a configuration enables accurate measurements.

Preferably, the size of the electrode may be equal to or smaller than the element area in consideration of a spread of an electric field created in the object by the element electrodes constituting the electrode, and the selector 111 changes the size of the electrode depending on the object. Such a configuration enables accurate measurements.

Preferably, each of the element electrodes constituting the electrode may include one or more electrode terminals, and the selector 111 may change the size and the shape of the electrode by selecting the one or more electrode terminals According to such a configuration, the electrical characteristic parameter inspection apparatus 1 can efficiently inspect an object having a wide region without mechanical scanning.

Preferably, each of the electrode terminals constituting the electrode may have a flat shape, a block shape, a film shape, a needle shape, or a flexible shape corresponding to a shape of the object. Such a configuration enables measurements appropriate for the shapes of objects.

Preferably, the multiple electrodes included in the selection pattern may be connected in parallel and be connected to the measurer 113. Such a configuration can adjust electrical characteristic parameters to be measured. More specifically, when an object has a high impedance, which is difficult to measure, the impedance to be measured can be decreased by connecting electrode pairs in parallel. This makes measurements easier.

Preferably, the multiple electrodes included in the selection pattern may be connected in series and be connected to the measurer 113. Such a configuration can adjust electrical characteristic parameters to be measured. More specifically, when an object has a low impedance, which is difficult to measure, the impedance to be measured can be increased by connecting electrode pairs in series. This makes measurements easier.

Preferably, between the electrodes constituting the selection pattern, a shielding area may be provided to reduce or prevent electrical interference between the electrodes. This increases accuracy of measurements.

Preferably, the shielding area may be formed by a second element electrode around a first element electrode that constitutes the electrode. Thus, the shielding area can be easily formed.

Preferably, the second element electrode may be an electrode connected to a ground. Thus, the shielding area can be formed.

Preferably, each of the selection patterns may form a predetermined two-dimensional pattern. Thus, the distribution of electrical characteristic parameters in the object C can be analyzed as two-dimensional information.

Preferably, the multiple selection patterns may be orthogonal to each other in a two-dimensional plane. Thus, the distribution of electrical characteristic parameters in the object C can be analyzed as two-dimensional information.

Preferably, the selector 111 may change the selection pattern; the measurer 113 may measure electrical characteristic parameters for the respective selection patterns selected by the selector 111; and the analyzer 114 may analyze the measured electrical characteristic parameters measured by the measurer 113. According to such a configuration, the electrical characteristic parameter inspection apparatus 1 can efficiently inspect an object having a wide region without mechanical scanning.

Preferably, the electric signal may be an AC signal; the signal generator 112 may control a frequency and/or an amplitude of the AC signal to be output; and the measurer 113 may measure an impedance or an admittance as the electrical characteristic parameter. According to such a configuration, the electrical characteristic parameter inspection apparatus 1 can efficiently inspect an object having a wide region without mechanical scanning.

Preferably, the electric signal may be a DC signal; the signal generator 112 may control a voltage and/or a current of the DC signal to be output; and the measurer 113 may measure an electrical resistance as the electrical characteristic parameter. According to such a configuration, the electrical characteristic parameter inspection apparatus 1 can efficiently inspect an object having a wide region without mechanical scanning.

Further, the electrical characteristic parameter inspection method includes: arranging two or more sensors on or over an object in a predetermined selection pattern among multiple selection patterns; measuring an electrical characteristic parameter output from the sensors arranged in the predetermined selection pattern; and analyzing the measured electrical characteristic parameter, wherein the measuring measures the electrical characteristic parameter each time the arranging changes the selection pattern, and the analyzing analyzes electrical characteristic parameters measured for the respective selection patterns. Such a method enables an efficient inspection of an object having a wide region without mechanical scanning.

Further, the electrical characteristic parameter inspection method includes: arranging an electrode pair on or over a front surface and/or a back surface of an object in a predetermined selection pattern among multiple selection patterns; measuring an electrical characteristic parameter by bringing electrodes included in the selection pattern into contact with or close to the object and by applying a predetermined electric signal to the object; and analyzing the measured electrical characteristic parameter, wherein the measuring measures the electrical characteristic parameter each time the arranging changes the selection pattern, and the analyzing analyzes electrical characteristic parameters measured for the respective selection patterns. Such a method enables an efficient inspection of an object having a wide region without mechanical scanning.

Further, a program causes a computer of an electrical characteristic parameter inspection apparatus that includes multiple sensors to be arranged on or over an object to function as: the selector 111 that selects multiple predetermined selection patterns, each of the selection patterns including two or more sensor pairs among the multiple sensors; the measurer 113 that measures electrical characteristic parameters for the respective selection patterns, the electrical characteristic parameters being output from the sensors included in the selection patterns; and the analyzer 114 that analyzes the electrical characteristic parameters measured for the respective selection patterns. Such a program enables an efficient inspection of an object having a wide region without mechanical scanning.

Further, a program causes a computer of an electrical characteristic parameter inspection apparatus that includes multiple electrode terminals to be arranged on or over a front surface and/or a back surface of an object to function as: the selector 111 that forms an electrode including at least one element electrode, the element electrode including two or more electrode terminals among the multiple electrode terminals, and that forms selection patterns each of which includes multiple electrodes; the signal generator 112 that outputs a predetermined electric signal; the measurer 113 that brings the electrodes included in each of the selection patterns into contact with or close to the object; and the analyzer 114 that applies the electric signal output by the signal generator 112 to the electrodes and that measures an electrical characteristic parameter; and the analyzer 114 that analyzes the electrical characteristic parameters measured for the respective selection patterns. Such a program enables an efficient inspection of an object having a wide region without mechanical scanning.

The above-described embodiments of the present invention are preferable examples of the present invention and not intended to limit the present invention.

For example, although the data obtainer 11 in the above embodiments uses machine learning to analyze electric field patterns and values of electrical characteristic parameters, machine learning is not essential Corrosion of inside rebars can be detected based on the change in values of electrical characteristic parameters measured for the respective electric field patterns.

Further, although the second electrode E2 in the out-plane arrangement is on the bottom surface of the object C in the above embodiments, the second electrode E2 may be provided inside the object C.

In the above description, a hard disk and a semiconductor nonvolatile memory are disclosed as examples of a computer readable medium that stores the program of the present invention. However, the computer readable medium is not limited to these examples. As the computer readable medium, a portable storage medium, such as a CD-ROM, can also be used.

Other detailed configurations and operations of the electrical characteristic parameter inspection apparatus can also be appropriately modified without departing from the scope of the present invention.

Although embodiments of the present invention have been described and illustrated in detail, the disclosed embodiments are made for purposes of illustration and example only and not limitation. The scope of the present invention should be interpreted by terms of the appended claims.

The invention claimed is:

1. An electrical characteristic parameter inspection apparatus comprising:
   multiple sensors to be arranged on or over an object; and
   a hardware processor that
      selects multiple predetermined selection patterns, each of the multiple predetermined selection patterns including a sensor pair, the sensor pair including two or more sensors among the multiple sensors;
      brings the sensor pair into contact with or close to the object and measures electrical characteristic parameters for the each of the multiple predetermined selection patterns, the electrical characteristic parameters being output from the sensors included in the each of multiple predetermined selection patterns; and
      analyzes the electrical characteristic parameters measured for the each of the multiple predetermined selection patterns.

2. An electrical characteristic parameter inspection apparatus comprising:
   multiple electrode terminals to be arranged on or over a front surface and/or a back surface of an object; and
   a hardware processor that
      forms an electrode, the electrode including at least two element electrodes, each of the element electrodes including at least one electrode terminal among the multiple electrode terminals, and forms selection patterns each of which includes multiple electrodes;
      outputs a predetermined electric signal;
      brings the electrodes included in each of the selection patterns into contact with or close to the object, applies the output electric signal to the electrodes, and measures an electrical characteristic parameter; and
      analyzes electrical characteristic parameters measured for the respective selection patterns.

3. The electrical characteristic parameter inspection apparatus according to claim 2, wherein
   based on an electrical characteristic of the object, the hardware processor determines a measurement target region of the object as an element area, the element area corresponding to the electrode, and measures the electrical characteristic parameter of the element area.

4. The electrical characteristic parameter inspection apparatus according to claim 3, wherein
   a size of the electrode is equal to or smaller than the element area in consideration of a spread of an electric field created in the object by the element electrodes constituting the electrode, and
   the hardware processor changes the size of the electrode depending on the object.

5. The electrical characteristic parameter inspection apparatus according to claim 2, wherein
   each of the element electrodes constituting the electrode includes one or more electrode terminals, and
   the hardware processor changes a size and a shape of the electrode by selecting the one or more electrode terminals.

6. The electrical characteristic parameter inspection apparatus according to claim 2, wherein
   each of the electrode terminals constituting the electrode has a flat shape, a block shape, a film shape, a needle shape, or a flexible shape corresponding to a shape of the object.

7. The electrical characteristic parameter inspection apparatus according to claim 2, wherein
   the multiple electrodes included in the selection pattern are connected in parallel and are connected to the hardware processor.

8. The electrical characteristic parameter inspection apparatus according to claim 2, wherein
   the multiple electrodes included in the selection pattern are connected in series and are connected to the hardware processor.

9. The electrical characteristic parameter inspection apparatus according to claim 2, wherein
   between the electrodes constituting the selection pattern, a shielding area is provided to reduce or prevent electrical interference between the electrodes.

10. The electrical characteristic parameter inspection apparatus according to claim 9, wherein
    the shielding area is formed by a second element electrode around a first element electrode that constitutes the electrode.

11. The electrical characteristic parameter inspection apparatus according to claim 10, wherein
    the second element electrode is connected to a ground.

12. The electrical characteristic parameter inspection apparatus according to claim 2, wherein
    each of the selection patterns forms a predetermined two-dimensional pattern.

13. The electrical characteristic parameter inspection apparatus according to claim 12, wherein
    the selection patterns are orthogonal to each other in a two-dimensional plane.

14. The electrical characteristic parameter inspection apparatus according to claim 2, wherein
    the hardware processor changes the selection pattern,
    the hardware processor measures electrical characteristic parameters for the respective selection patterns, and
    the hardware processor analyzes the measured electrical characteristic parameters.

15. The electrical characteristic parameter inspection apparatus according to claim 2, wherein
    the electric signal is an AC signal, and the hardware processor controls a frequency and/or an amplitude of the AC signal to be output and measures an impedance or an admittance as the electrical characteristic parameter.

16. The electrical characteristic parameter inspection apparatus according to claim 2, wherein the electric signal is a DC signal, and the hardware processor controls a voltage and/or a current of the DC signal to be output and measures an electrical resistance as the electrical characteristic parameter.

17. An electrical characteristic parameter inspection method comprising:

arranging two or more sensors on or over an object in a predetermined selection pattern among multiple selection patterns;

bringing the sensors arranged in the predetermined selection pattern into contact with or close to the object;

measuring an electrical characteristic parameter output from the sensors arranged in the predetermined selection pattern; and analyzing the measured electrical characteristic parameter, wherein the measuring measures the electrical characteristic parameter for each of the multiple selection patterns, and the analyzing analyzes electrical characteristic parameters measured for the multiple selection patterns.

18. An electrical characteristic parameter inspection method comprising:

arranging an electrode pair on or over a front surface and/or a back surface of an object in a predetermined selection pattern among multiple selection patterns;

measuring an electrical characteristic parameter by bringing electrodes included in the predetermined selection pattern into contact with or close to the object and by applying a predetermined electric signal to the object; and analyzing the measured electrical characteristic parameter, wherein the measuring measures the electrical characteristic parameter for each of the multiple selection patterns, and the analyzing analyzes electrical characteristic parameters measured for the multiple selection patterns.

19. A nontransitory computer-readable storage medium storing a program for a computer of an electrical characteristic parameter inspection apparatus that includes multiple sensors to be arranged on or over an object, the program causing the computer to:

select multiple predetermined selection patterns, each of the multiple predetermined selection patterns including two or more sensor pairs among the multiple sensors;

bring the two or more sensor pairs in the each of the multiple predetermined selection patterns into contact or close to the object, and measure electrical characteristic parameters for the each of the multiple predetermined selection patterns, the electrical characteristic parameters being output from sensors included in each of the multiple predetermined selection patterns; and analyze the electrical characteristic parameters measured for the each of the multiple predetermined selection patterns.

20. A nontransitory computer-readable storage medium storing a program for a computer of an electrical characteristic parameter inspection apparatus that includes multiple electrode terminals to be arranged on or over a front surface and/or a back surface of an object, the program causing the computer to:

form an electrode including at least one element electrode, the element electrode including two or more electrode terminals among the multiple electrode terminals, and form selection patterns each of which includes multiple electrodes;

output a predetermined electric signal;

bring the electrodes included in each of the selection patterns into contact with or close to the object, apply the output electric signal to the electrodes, and measure an electrical characteristic parameter; and analyze electrical characteristic parameters measured for the respective selection patterns.

* * * * *